(12) United States Patent
Chung et al.

(10) Patent No.: US 12,091,465 B2
(45) Date of Patent: Sep. 17, 2024

(54) COMPOSITION FOR PREVENTING OR TREATING DISEASES CAUSED BY OVEREXPRESSION OF CHEMOKINE $CX_3CL1$, CONTAINING DEATH RECEPTOR INHIBITOR AS ACTIVE INGREDIENT

(71) Applicant: Seoul National University R&DB Foundation, Seoul (KR)

(72) Inventors: Doo Hyun Chung, Seoul (KR); Eugene C. Yi, Seoul (KR); Dongjin Jeong, Seoul (KR); Min Jueng Kang, Seoul (KR); Donghyun Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 908 days.

(21) Appl. No.: 16/637,357

(22) PCT Filed: Aug. 14, 2018

(86) PCT No.: PCT/KR2018/009351
§ 371 (c)(1),
(2) Date: Feb. 7, 2020

(87) PCT Pub. No.: WO2019/035646
PCT Pub. Date: Feb. 21, 2019

(65) Prior Publication Data
US 2023/0159650 A1    May 25, 2023

(30) Foreign Application Priority Data
Aug. 17, 2017 (KR) .......... 10-2017-0104381

(51) Int. Cl.
| | | |
|---|---|---|
| *C07K 14/705* | (2006.01) | |
| *A61P 19/02* | (2006.01) | |
| *C07K 14/71* | (2006.01) | |
| *C07K 16/28* | (2006.01) | |
| *C12N 15/113* | (2010.01) | |
| *G01N 33/68* | (2006.01) | |
| *A61K 39/00* | (2006.01) | |

(52) U.S. Cl.
CPC .......... *C07K 16/2878* (2013.01); *A61P 19/02* (2018.01); *C07K 14/70578* (2013.01); *C07K 14/70596* (2013.01); *C12N 15/113* (2013.01); *C12N 15/1138* (2013.01); *G01N 33/6872* (2013.01); *A61K 2039/505* (2013.01); *C12N 2310/11* (2013.01); *C12N 2310/14* (2013.01); *G01N 2333/70578* (2013.01)

(58) Field of Classification Search
CPC .......... A61K 2039/505; A61K 39/3955; A61P 19/02; C12N 15/1138; C12N 15/113; C12N 2310/11; C12N 2310/16; C12N 2310/141; C12N 2310/14; C07K 16/28; C07K 16/2896; C07K 14/70596; C07K 14/71; C07K 14/70578
See application file for complete search history.

(56) References Cited

U.S. PATENT DOCUMENTS

| | | | |
|---|---|---|---|
| 8,067,001 B2 | 11/2011 | Zhou et al. | |
| 2001/0029030 A1* | 10/2001 | Alnemri ............. | C07K 14/7151 |
| | | | 435/7.1 |
| 2005/0112666 A1 | 5/2005 | Browning et al. | |
| 2005/0159357 A1 | 7/2005 | Hurez et al. | |
| 2016/0297865 A1* | 10/2016 | Walczak .......... | G01N 33/57492 |
| 2018/0050090 A1* | 2/2018 | Lee ........................ | A61K 47/36 |

FOREIGN PATENT DOCUMENTS

| | | |
|---|---|---|
| KR | 10-2004-0081422 | 9/2004 |
| KR | 10-2007-0010046 | 1/2007 |
| KR | 10-2007-0102585 | 10/2007 |
| KR | 10-2008-0004339 | 1/2008 |
| KR | 10-2010-0045903 | 5/2010 |
| KR | 10-2014-0032407 | 3/2014 |

OTHER PUBLICATIONS

Kurbanov et al. Efficient TRAIL-R1/DR4-mediated apoptosis in melanoma cells by tumor necrosis factor-related apoptosis-inducing ligand (TRAIL). J Invest Dermatol 125: 1010-1019, 2005.*
Christensen et al. K/BxN Serum-Transfer Arthritis as a Model for Human Inflammatory Arthritis. Front Immunol 7: 213, 2016 (17 total pages).*
Donghyun et al. Soluble Fas ligand activates the CX3CL1-CX3CR1 axis by enhancing proteinase activity during arthritis in Fas-independent manner (HUM7P.312) J Immunol 192 (1 Suppl): 184.21, 2014.*
Kim et al. Effective Treatment of Established Mouse Collagen-Induced Arthritis by Systemic Administration of Dendritic Cells Genetically Modified to Express FasL. Mol Ther 6(5): 584-590, 2002.*
Li et al. Anti-DR5 mAb Ameliorate Adjuvant Arthritis Rats Through Inducing Synovial Cells Apoptosis. Exp Biol Med 234: 1468-1476, 2009.*
Liu et al., Death Receptor Regulation and Celecoxib-Induced Apoptosis in Human Lung Cancer Cells.J Natl Cancer Instit 96(23): 1769-1780, 2004.*
Liu et al. Role of CX3CL1 in Diseases. Arch Immunol Ther Exp 64: 371-383, 2016.*

(Continued)

*Primary Examiner* — Bridget E Bunner
(74) *Attorney, Agent, or Firm* — LEX IP MEISTER, PLLC

(57) ABSTRACT

The present invention relates to a composition for preventing or treating diseases caused by overexpression of chemokine $CX_3CL1$ (fractalkine) comprising a death receptor 5 (DR5) inhibitor as an active ingredient, a method for preventing or treating diseases caused by overexpression of chemokine $CX_3CL1$ comprising administering a DR5 expression or activity inhibitor to a patient in need of prevention or treatment of diseases caused by overexpression of chemokine $CX_3CL1$ in a therapeutically effective amount, and a use for prevention or treatment of diseases caused by overexpression of chemokine $CX_3CL1$ of a DR5 expression or activity inhibitor.

1 Claim, 9 Drawing Sheets
Specification includes a Sequence Listing.

(56) References Cited

OTHER PUBLICATIONS

MacFarlane et al. Identification and Molecular Cloning of Two Novel Receptors for the Cytotoxic Ligand TRAIL. J Biol Chem 272(41): 25417-25420, 1997.*

Monarch et al. The K/BxN Arthritis Model. Curr Protoc Immunol 81: 15.22.1-15.22.12, 2008.*

Oh et al. Suppression of death receptor 5 enhances cancer cell invasion and metastasis through activation of caspase-8/TRAF2-mediated signaling. Oncotarget 6(38): 41324-41338, 2015.*

Ren et al. Differential Regulation of the TRAIL Death Receptors DR4 and DR5 by the Signal Recognition Particle. Mol Biol Cell 15: 5064-5074, 2004.*

Song et al. Tumor Necrosis Factor-related Apoptosis-inducing Ligand (TRAIL) Is an Inhibitor of Autoimmune Inflammation and Cell Cycle Progression. J Exp Med 191(7): 1095-1103, 2000.*

Van Geelan et al. Modulation of TRAIL resistance in colon carcinoma cells: Different contributions of DR4 and DR5. BMC Cancer 11 : 39, 2011 (13 total pages).*

White et al. Cancer Prevention for the next generation. J Adolesc Health 52: S1-S7, 2013.*

PCT Search Report & Written Opinion of Application No. PCT/KR2018/009351, Nov. 27, 2018.

NCBI, tumor necrosis factor receptor superfamily member 10B isoform 2 precursor [*Homo sapiens*], GenBank Accession No. NP_671716.2, Apr. 9, 2017, Apr. 9, 2017.

Ichikawa et al. "TRAIL-R2 (DR5) Mediates Apoptosis of Synovial Fibroblasts in Rheumatoid Arthritis", The Journal of Immunology, 2003, 171(2): 1061-1069.

Miranda-Carus et al. "Rheumatoid Arthritis Synovial Fluid Fibroblasts Express TRAIL-R2 (DR5) That Is Functionally Active", Arthritis and Rheumatism, vol. 50, No. 9, pp. 2786-2793, Sep. 2004.

Martinez-Lostao et al. "Targeting the Apo2L/TRAIL system for the therapy of autoimmune diseases and cancer", Biochemical Pharmacology, 83 pp. 1475-1483, Jan. 2012.

Varfolomeev et al., "Molecular Determinants of Kinase Pathway Activation by Apo2 Ligand/Tumor Necrosis Factor-related Apoptosis-inducing Ligand", Journal of Biological Chemistry, Oct. 2005, 280(49): 40599-40608.

Sarah G. Hymowitz et al., "Triggering Cell Death: The Crystal Structure of Apo2L/TRAIL in a Complex with Death Receptor 5", Molecular Cell, vol. 4, 563-571, Oct. 1999.

Qiao et al. "Structural basis of LaDR5, a novel agonistic anti-death receptor 5 (DR5) monoclonal antibody, to inhibit DR5/TRAIL complex formation", BMC Immunology 13:40, 2012.

Wanhu Tang et al., "TRAIL receptor mediates inflammatory cytokine release in an NF-κB-dependent manner", Cell Research 19:758-767, May 2009.

Ashkenazi, "Targeting Death and Decoy Receptors of the Tumournecrosis Factor Superfamily", Nature Reviews Cancer vol. 2, Jun. 2002, 19: 758-767.

Minji Jo et al., "Apoptosis induced in normal human hepatocytes by tumor necrosis factor-related apoptosis-inducing ligand", Nature Medicine vol. 6 No. 5, May 2000, pp. 564-567.

McComb et al., "CX3CL1 Up-Regulation Is Associated with Recruitment of CX3CR1 Mononuclear Phagocytes and T Lymphocytes in the Lungs during Cigarette Smoke-Induced Emphysema", American Journal of Pathology vol. 173, No. 4, Oct. 2008.

Hasegawa et al., "Up regulated expression of fractalkine/CX3CL1 and CX3CR1 in patients with systemic sclerosis",—Annals of the Rheumatic Diseases, 2005, 64: 21-28.

Echigo et al., "Expression of fractalkine and its receptor, CX3CR1, in atopic dermatitis: Possible contribution to skin inflammation", Journal of Allergy and Clinical Immunology, 2004, 113: 940-948.

Inoue et al. "Antagonist of Fractalkine (CX3CL1) Delays the Initiation and Ameliorates the Progression of Lupus Nephritis in MRL/lpr Mice", Arthritis and Rheumatism vol. 52, No. 5, pp. 1522-1533, May 2005.

* cited by examiner

FIG. 7a

Protein

MEQRG QNAPA ASGAR KRHGP GPREA RGARP GPRVP KTLVL VVAAV LLVSA

ESALI TQQDL APQQR AAPQQ KRSSP SEGLC PPGHH ISEDG RDCIS CKYGQ

DYSTH WNDLL *FCLRC* T*RCDS* GEVEL SPCTT TRNTV CQCEE GT*FRE* ED*SPE*  huDR5-CRD3
                  A A    AA  huDR5-CRD2                             A A

MCRKC *R*TGCP RGMVK VGDCT PWSDI ECVHK ESGII IGVTV AAVVL IVAVF
  A  A

VCKSL LWKKV LPYLK GICSG GGGDP ERVDR SSQRP GAEDN VLNEI VSILQ

PTQVP EQEME VQEPA EPTGV NMLSP GESEH LLEPA EAERS QRRRL LVPAN

EGDPT ETLRQ CFDDF ADLVP FDSWE PLMRK LGLMD NEIKV AKAEA AGHRD

TLYTM LIKWV NKTGR DASVH TLLDA LETLG ERLAK QKIED HLLSS GKFMY

LEGNA DSAMS

FIG. 7b

```
   1 atggaacaac ggggacagaa cgccccggcc gcttcggggg cccggaaaag gcacggccca
  61 ggacccaggg aggcgcgggg agccaggcct gggccccggg tccccaagac ccttgtgctc
 121 gttgtcgccg cggtcctgct gttggtctca gctgagtctg ctctgatcac caacaagac
 181 ctagctcccc agcagagagc ggccccacaa caaaagaggt ccagcccctc agagggattg
 241 tgtccacctg gacaccatat ctcagaagac ggtagagatt gcatctcctg caaatatgga
 301 caggactata gcactcactg gaatgacctc cttttctgct tgcgctgcac caggtgtgat
                                           GCCTGCT TGGCCTGCAC CGCGTGTGCT   ⎤ huO85-CDR2
 361 tcaggtgaag tggagctaag tccctgcacc acgaccagaa acacagtgtg tcagtgcgaa  ⎦
                                                                     GCA
 421 gaaggcacct tccgggaaga agattctcct gagatgtgcc ggaagtgccg cacagggtgt   ⎤ huO85-CDR3
                     GCTCCT GCGATGTGCG CGAAGTGCGC C                       ⎦
 481 cccagaggga tggtcaaggt cggtgattgt cacccctgga gtgacatcga atgtgtccac
 541 aaagaatcag gcatcatcat aggagtcaca gttgcagccg tagtcttgat tgtggctgtg
 601 tttgtttgca agtctttact gtggaagaaa gtccttcctt acctgaaagg catctgctca
 661 ggtggtggtg gggaccctga gcgtgtggac agaagctcac aacgacctgg ggctgaggac
 721 aatgtcctca atgagatcgt gagtatcttg cagcccaccc aggtccctga gcaggaaatg
 781 gaagtccagg agccagcaga gccaacaggt gtcaacatgt tgtcccccgg ggagtcagag
 841 catctgctgg aaccggcaga agctgaaagg tctcagagga ggaggctgct ggttccagca
 901 aatgaaggtg atcccactga gactctgaga cagtgcttcg atgactttgc agacttggtg
 961 ccctttgact cctgggagcc gctcatgagg aagttgggcc tcatggacaa tgagataaag
1021 gtggctaaag ctgaggcagc gggccacagg acaccttgt acacgatgct gataaagtgg
1081 gtcaacaaaa ccgggcgaga tgcctctgtc cacaccctgc tggatgcctt ggagacgctg
1141 ggagagagac ttgccaagca agattgag gaccacttgt tgagctctgg aaagttcatg
1201 tatctagaag gtaatgcaga ctctgccatg tcctaa
```

FIG. 8a

Fas/DR5 transfection→FaL-igG staining

Protein

MEQRG QNAPA ASGAR KRHGP GPREA RGARP GPRVP KTLVL VVAAV LLVSA

ESALI TQQDL APQQR AAPQQ KRSSP SEGLC PPGHH ISEDG RDCIS CKYGQ

DYSTH WNDLL FCLRC TRCDS GEVEL SPCTT TRNTV CQCEE GTFRE EDSPE  huDR5-CRD3
                A  A    AA    huDR5-CRD2                           A A

MCRKC RTGCP RGMVK VGDCT PWSDI ECVHK ESGII IGVTV AAVVL IVAVF
    A  A

VCKSL LWKKV LPYLK GICSG GGGDP ERVDR SSQRP GAEDN VLNEI VSILQ

PTQVP EQEME VQEPA EPTGV NMLSP GESEH LLEPA EAERS QRRRL LVPAN

EGDPT ETLRQ CFDDF ADLVP FDSWE PLMRK LGLMD NEIKV AKAEA AGHRD

TLYTM LIKWV NKTGR DASVH TLLDA LETLG ERLAK QKIED HLLSS GKFMY

LEGNA DSAMS               Immunogen for DR5 FACS antibody

COMPOSITION FOR PREVENTING OR TREATING DISEASES CAUSED BY OVEREXPRESSION OF CHEMOKINE CX₃CL1, CONTAINING DEATH RECEPTOR INHIBITOR AS ACTIVE INGREDIENT

INCORPORATION BY REFERENCE OF SEQUENCE LISTING

This application contains a Sequence Listing in computer readable form (filename: LPP20194712US_sequence_listing.txt: 16,257 bytes; created Jan. 10, 2024), which is incorporated herein by reference in its entirety and forms part of the disclosure.

TECHNICAL FIELD

The present invention relates to a composition for preventing or treating diseases caused by overexpression of chemokine $CX_3CL1$ (fractalkine) comprising a death receptor 5 (DR5) inhibitor as an active ingredient, and it can reduce expression of chemokine $CX_3CL1$ by inhibiting binding of FasL and DR5 on a cell surface using an agent controlling DR5 expression or activity, for example using an inhibitor, and thereby it can effectively prevent and treat diseases caused by overexpression of chemokine $CX_3CL1$.

BACKGROUND ART

Recently, as a target substance of cancer therapeutic agent development, the apoptosis route through TNF-related apoptosis inducing ligand (TRAIL or Apo2L) which selectively induces apoptosis of cancer cells only without affecting normal cells, and one of its receptors, DR5 (death receptors 5) system has been considered important (Ashkenazi et al., Nat Rev Cancer 2: 420, 2002). Currently, as a cancer cell therapeutic agent targeting DR5, recombinant TRAIL and apoptosis receptor-specific antibodies have been developed.

However, TRAIL has a problem of low specificity for DR5, since it binds to DR4 (Death receptor 4, TRAIL-Receptor 1), and DR5 (Death receptor 5, TRAIL-Receptor 2) which deliver apoptosis signals, as well as DcR1(Decoy Receptor 1, TRAIL-Receptor 3) and DcR2(Decoy Receptor 1, TRAIL-Receptor 4) which cannot deliver apoptosis signals. In addition, recombinant TRAIL is less stable and has side effects that cause apoptosis in normal cells such as astrocytes, hepatocytes, keratinocytes, and the like (Jo et al., Nature Medicine 6, 564-567, 2000).

Therefore, in recent years, the development of anti-DR5 to anti-DR4 antibodies which induce cancer cell selective apoptosis has been actively studied.

However, until now, research has focused on the development of cancer cell therapeutic agents using the apoptosis route though the DR5 system, and there have been no specific studies on the mechanism inducing inflammation of DR5 and the development of inflammation therapeutic agents using the same.

Fas ligands (FasL, CD95L, CD178, Apo-1) are one of Type II membrane protein, which belong to the tumor necrosis factor (TNF) system with TNF, CD40L, 4-1BBL and the like, and are mainly expressed in immune privileged sites such as activated T cells, NK cells, tumor cells and eyeballs and the like. Fas ligand (hereinafter, FasL) has a homotrimer structure, and is known to kill target cells through trimerization with Fas receptor (Fas; FasR; CD95; UniProt P25445), which is its receptor.

FasL can be divided into membrane FasL and soluble FasL (sFasL). Since apoptosis is induced by cell-cell contact, the membrane FasL plays a role in killing cells by forming a death inducing signaling complex (DISC) with Fas. sFasL is a cleavage of membrane FasL cut by serine matrix metalloproteinase-3 or -7 (MMP-3 or MMP-7), and has been known to inhibit apoptosis of target cells as opposed to function of membrane FasL, or function as a chemoattractant depending on the cellular microenvironment.

There are few reports on the specific role of FasL in inflammatory diseases, particularly, rheumatoid arthritis (RA). As fas as is known, as the result of comparing the amount of sFasL in Rap patients and Osteoarthritis patients, the amount of sFasL is increased in RA patients, and this is the only report that has been shown to play a role in inhibiting angiogenesis by reducing VEGF secreted from synovial fibroblasts. On the other hand, with respect to membrane FasL, there has been a report that apoptosis through Fas-FasL inhibits production of autoreactive cells in the early stage of rheumatoid arthritis to play a role in alleviating rheumatoid arthritis, in the CIA (collagen induced arthritis) model.

Considering that chemokine plays an important role in occurrence of various diseases, research on the development of an chemokine inhibitor which can effectively prevent or treat various diseases caused by chemokine and a therapeutic agent using the same is important, and in addition, specifically, it is necessary to reveal the mechanism inducing diseases such as inflammation of chemokine in cells and develop a therapeutic agent targeting a new target with excellent effects. However, specific research results are still insignificant.

DISCLOSURE

Technical Problem

Accordingly, the present inventors have newly determined the use of inhibiting expression of chemokine $CX_3CL1$ of a modulator which inhibits the activity or expression of DR5 inhibitor, thereby providing a composition for preventing or treating diseases caused by overexpression of chemokine $CX_3CL1$ and a composition for inhibiting expression of chemokine $CX_3CL1$, which contain a modulator that inhibits the activity or expression of DR5 inhibitor as an active ingredient.

Another embodiment provides a method of screening a modulator of chemokine expression and a therapeutic agent for diseases caused by overexpression of chemokine $CX_3CL1$, targeting DR5 protein.

Other embodiment relates to a method for preventing and/or treating diseases caused by overexpression of chemokine $CX_3CL1$ comprising administering an inhibitor of expression or activity of DR5 to a patient in need of prevention and/or treatment of diseases caused by overexpression of chemokine $CX_3CL1$ in a therapeutically effective amount.

Other embodiment provides a use for prevention and/or treatment of diseases caused by overexpression of chemokine $CX_3CL1$ of a DR5 expression or activity inhibitor.

Technical Solution

The present invention provides an effective prevention and treatment method of diseases caused by overexpression of chemokine $CX_3CL1$, by reducing expression of $CX_3CL1$ that is one of inflammatory cytokines, by inhibiting binding FasL and DR5 on a cell surface, using an agent, for example, an inhibitor, which controls expression or activity of death receptor 5 (DR5).

Accordingly, the present invention provides a method for preventing and/or treating diseases caused by overexpression of chemokine $CX_3CL1$, comprising administering an inhibitor of expression or activity of DR5 in a therapeutically effective amount to a patient in need of prevention and/or treatment of diseases caused by overexpression of chemokine $CX_3CL1$. Another embodiment provides a use for preventing and/or treating diseases caused by overexpression of chemokine $CX_3CL1$ of an inhibitor of expression or activity of DR5.

DR5 is also called TRAIL receptor 2 (TRAILR2) or tumor necrosis factor receptor superfamily member 10B (TNFRSF10B), and is a cell surface receptor of TNF-receptor superfamily binding to TRAIL and delivers apoptosis signals to mediate apoptosis. DR5 is known to interact with Caspase 8, Caspase 10, FADD (Fas-Associated protein with Death Domain), TRAIL, and the like. The DR5 may be derived from mammals, and for example, it may be human DR5 (e.g., NCBI accession no. UniProtKB/Swiss-Prot: Q6FH58 etc.)

One specific embodiment of the present invention provides a composition for preventing or treating diseases caused by overexpression of chemokine $CX_3CL1$ containing an inhibitor of expression or activity of DR5 as an active ingredient.

The kind of the inhibitor of expression or activity of DR5 is not particularly limited, but it means all substances acting reducing, removing and/or blocking actions of DR5 including reducing or removing the activity of DR5, and inhibiting, removing and inactivating expression of DR5. For example, it may be one or more kinds selected from the group consisting of siRNA, shRNA, miRNA, ribozyme, DNAzyme, PNA (peptide nucleic acids), anti-sense oligonucleotide, peptide, an antibody, an aptamer, natural extract or a chemical substance or the like, and preferably, the antibody or siRNA may be used.

According to one embodiment of the present invention, the inhibitor of expression or activity of DR5 may bind to a CRD2 domain of DR5, or a CRD3 domain of DR5, or both a CRD2 domain and a CRD3 domain.

According to another embodiment of the present invention, the antibody may bind to the 53rd to 181th amino acid part in the amino acid sequence of SEQ ID NO: 1 as an antigen.

Preferably, the antibody may bind to a CRD2 domain of DR5 consisting of the 101th to 120th amino acid sequence of SEQ ID NO: 1, or a CRD3 domain of DR5 consisting of the 143th to 160th amino acid sequence of SEQ ID NO: 1, or both the CRD2 and CRD3 domains, and for example, it may be an antibody binding to a CRD2 domain of huDR5 or a CRD3 domain of huDR5, respectively, as an antigen epitope.

According to one embodiment of the present invention, the siRNA may be siRNA binding to a sequence encoding CRD2 domain of DR5 consisting of the 301st to 363th sequence of SEQ ID NO: 4, or a sequence encoding CRD3 domain of DR5 consisting of the 430th to 483th sequence of SEQ ID NO: 4, or both a sequence encoding CRD2 domain of DR5 and a sequence encoding CRD3 domain of DR5. Preferably, it may be siRNA binding to each of the sequence encoding CRD2 domain of DR5 and the sequence encoding CRD3 domain of DR5 to inhibit expression of CRD2 and CRD3 of DR5.

The chemokine $CX_3CL1$ is called fractalkine (FKN), and is known as chemokine (C—$X_3$—C motif) ligand 1, and is a chemokine involved in causing inflammation. $CX_3CL1$ is a unique type of chemokine which comprises an extracellular N-terminal domain, mucin-like stalk, transmembrane αhelix and short intracytoplasmic tail, and consists of 373 amino acids. In particular, an aqueous type of $CX_3CL1$ is known to show chemotactic activity in monocytes, NK cells and T cells. In addition, $CX_3CL1$ is expressed in macrophages, fibroblasts, endotheliocytes, and dendritic cells in rheumatoid arthritis (RA) synovial tissue, and acts as an adhesive molecule in white blood cells, and enhances extravasation of white blood cells through an endothelium. In addition, $CX_3CL1$ induced by TNF-α, IFN-γ, and IL-1β is known to be related to scleroma, rheumatoid arthritis (RA), HIV infection, cancer and other various diseases, complications, and the like, but until now, there is no clinical therapeutic method targeting $CX_3CL1$.

The kinds of the diseases caused by overexpression of chemokine $CX_3CL1$ are not particularly limited, but it may be one or more kinds selected from the group consisting of arthritis, cardiovascular disease, cancer, HIV infection, primary biliary cirrhosis, renal disorder, allograft rejection, hypertension, eye disease, chronic pancreatitis, neuropathic pain, Sjogren's syndrome, chronic obstructive pulmonary disease and emphysema (COPD and emphysema; Am J Pathol. 2008 October; 173(4):949-61), pulmonary fibrosis (Ann Rheum Dis. 2005 January; 64(1):21-8.), atopic dermatitis (J Allergy Clin Immunol. 2004 May; 113(5):940-8), and Lupus nephritis (Arthritis Rheum. 2005 May; 52(5): 1522-33.), and in particular, it may be one of arthritis, cardiovascular disease, cancer, and HIV infection, and preferably, it may be arthritis.

Specifically, the arthritis may be osteoarthritis, degenerative arthritis, desquamative osteoarthritis, articular ligament damage, meniscal damage, joint malalignment, avascular necrosis, rheumatoid arthritis, juvenile idiopathic arthritis, trauma, inflammatory arthritis or arthritis caused by infection.

On the other hand, the cardiovascular diseases may be atherosclerosis, coronary artery disease, carotid artery disease, stroke or carotid atherosclerosis, and the cancer may be a colorectal cancer or lung cancer.

The composition for preventing or treating diseases may further comprise one or more of adjuvants selected from the group consisting of a carrier, an excipient, a disintegrating agent, a sweetener, a coating material, an inflating agent, a lubricant, a glydent, a flavoring agent, an antioxidant, a buffer solution, a bacteriostatic agent, a diluent, a dispersing agent, a surfactant, a binding agent and a lubricant.

Specifically, the carrier, excipient and diluent may be lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate, and mineral oil, and solid preparations for oral administration include tablets, pills, powder, granules, capsules, and the like, and such solid preparations may be prepared by mixing at least one of excipients, for example, starch, calcium carbonate, sucrose or lactose, gelatin, and the like to the composition. In addition, other than simple excipients, lubricants such as magnesium stearate and talc may be used. Liquid preparations for oral administration include suspension, oral liquids, emulsion and syrup and the like, and various excipients in addition to the commonly used simple diluent, water and liquid paraffin, for example, a wetting agent, a sweetener, a flavoring agent, a preservative and the like may be comprised. Preparations for parenteral administration include a sterile aqueous solution, a non-aqueous solvent, suspension, emulsion, a lyophilized preparation, a suppository and the like. As the suspension, propylene glycol, polyethylene glycol, plant oil such as olive oil, injectable ester such as ethyl oleate and the like may be used. As a base material of the suppository, witepsol, macrogol, tween 61, cacao butter, laurin butter, glycerogelatin and the like may be used.

The formulation of the composition is not particularly limited, but the kind may be selected from the group consisting of granules, powder, coating tablets, tablets, pills, capsules, suppositories, gel, syrup, juice, suspension, emulsion, drops or liquids.

The range of the effective dose of the composition of the present invention may differ according to various factors such as gender, severity, age, administration method, target cell and expression level, and the like, and it may be easily determined by those skilled in the art.

Furthermore, the present inventors have confirmed that the amount of intracellular $CX_3CL1$ is increased when FasL and DR5 bind specifically as FasL-DR5 binding, differently from it when TRAIL commonly known as a ligand binding to DR5 is treated for TRAIL-DR5 binding reaction, through a specific experiment (See Example 4 as follows). In addition, it has been confirmed that the amount of secreted $CX_3CL1$ is decreased, when an anti-DR5 antibody, or siRNA for knocking-down DR5 gene is treated to FasL-DR5 to interrupt formation of FasL-DR5 complexes (See Example 5 as follows).

In other words, the present inventors have found that the expression of intracellular chemokine $CX_3CL1$ can be significantly inhibited when an inhibitor of expression or activity of DR5 is treated, and as aforementioned, they have found that the inhibitor of expression or activity of DR5 can be used as an active ingredient of the composition for preventing and treating diseases caused by overexpression of $CX_3CL1$ (See Example 6).

Based on the findings, in one other embodiment of the present invention, a composition for inhibiting expression of chemokine $CX_3CL1$ containing an inhibitor of expression or activity of DR5 as an active ingredient is provided.

DR5 protein binds to FasL and increases expression of intracellular $CX_3CL1$, and thus when the inhibitor of DR5 expression or activity of the present invention is treated, the expression of intracellular $CX_3CL1$ may be significantly inhibited.

The kinds of the DR5 inhibitor are not particularly limited, but it may be one or more kinds selected from the group consisting of siRNA, shRNA, miRNA, ribozyme, DNAzyme, PNA (peptide nucleic acids), anti-sense oligonucleotide, peptide, an antibody, an aptamer, natural extract or a chemical substance or the like, and preferably, an antibody or siRNA may be used.

According to one embodiment of the present invention, the inhibitor of expression or activity of DR5 may bind to a CRD2 domain of DR5, or a CRD3 domain of DR5, or both a CRD2 domain and a CRD3 domain.

According to one other embodiment of the present invention, the antibody may bind to the 53th to 181th amino acid part in the amino acid sequence of SEQ ID NO: 1 as an antigen.

Preferably, the antibody may bind to a CRD2 domain of DR5 consisting of the 101th to 120th amino acid sequence of SEQ ID NO: 1, or a CRD3 domain of DR5 consisting of the 143th to 160th amino acid sequence of SEQ ID NO: 1, or both the CRD2 and CRD3 domains, and for example, it may be an antibody binding to each of a CRD2 domain of DR5 or a CRD3 domain of huDR5 as an antigen epitope.

According to one embodiment of the present invention, the siRNA may be siRNA binding to a sequence encoding CRD2 domain of DR5 consisting of the 301th to 363th sequence of SEQ ID NO: 4, or a sequence encoding CRD3 domain of DR5 consisting of the 430th to 483th sequence of SEQ ID NO: 4, or both a sequence encoding CRD2 domain of DR5 and a sequence encoding CRD3 domain of DR5. Preferably, it may be siRNA binding to each of the sequence encoding CRD2 domain of DR5 and the sequence encoding CRD3 domain of DR5 to inhibit expression of CRD2 and CRD3 of DR5.

In addition, in other specific embodiment of the present invention, provided is
a screening method of an inhibitor of chemokine expression, comprising
reacting a candidate substance to a sample; and
measuring the DR5 activity or expression of the sample,
and comprising determining the candidate substance as an inhibitor of expression of chemokine $CX_3CL1$, when the activity or expression of DR5 in the sample treated with the candidate substance is decreased than DR5 in the sample not treated with the candidate substance.

The inhibitor of expression of chemokine $CX_3CL1$ selected by the screening method may be used as a prophylactic agent and/or a therapeutic agent for diseases caused by overexpression of chemokine $CX_3CL1$ such as arthritis, cardiovascular diseases, cancer, HIV infection, primary biliary cirrhosis, renal disorder, allograft rejection, hypertension, eye disease, chronic pancreatitis, neuropathic pain, Sjogren syndrome, chronic obstructive pulmonary disease, emphysema, pulmonary fibrosis, atopic dermatitis, and lupus nephritic, and the like. Therefore, the screening method may be a screening method of a prophylactic agent and/or a therapeutic agent for diseases caused by overexpression of chemokine $CX_3CL1$.

The sample may be an animal, preferably, a cell, tissue or organ obtained from a mammal, and preferably, may include RA (Rheumatoid arthritis) sites, immune privileged sites, and the like, and more preferably, T cells, NK cells, rheumatoid cells, tumor cells or eyeballs or the like.

The activity of DR5 may be measured by common methods, and this can be easily seen by those skilled in the art. For example, confirmation of the reaction between DR5 and the sample may use methods commonly used for confirming the reaction between protein-protein or between protein-compound. For example, a method for measuring the activity after reacting DR5 and a test subject substance, yeast two hybrid, a screening method using HTS (high throughput screening) using search of phage display peptide clones binding to DR5, natural products and chemical substances library, and the like, drug hit HTS or cell-based screening, or the like, but not limited to these methods.

Moreover, the expression of DR5 may be measured by confirming the reaction between a composition comprising a gene encoding DR5 and a sample, and the reaction confirmation may use commonly used methods for confirming the reaction between DNA-DNA, DNA-RNA and DNA-protein. For example, in vitro, a hybridization test for confirming binding between the gene and test subject substance, a method for measuring the expression rate of the gene through northern analysis after reacting a mammal cell and a test subject substance, or a method for connecting a reporter gene to the gene to introduce it inside of a cell and then reacting it with a test subject substance to measure the expression rate of the reporter protein, or the like may be used, but not limited to these methods.

In the screening method of the present invention, the sample may be estimated to have possibility to prevent or treat diseases caused by overexpression of chemokine $CX_3CL1$ (fractalkine) according to the common selection method, or may be randomly selected respective nucleic acid, protein, other extract or natural products, compounds, or the like.

Substances obtained by this screening method have advantages of having a prophylactic effect of occurrence and a therapeutic effect in the early stage of occurrence of diseases caused by overexpression of chemokine $CX_3CL1$, as well as excellent effects of alleviating and treating disease conditions in the middle and end stages with some progress, and may act as a leading compound in the process of development of a prophylactic or therapeutic agent for diseases caused by overexpression of chemokine $CX_3CL1$. By modifying and optimizing the structure of the leading compound, a new therapeutic agent may be developed, and this substance exhibits an inhibitory effect of expression of $CX_3CL1$ by inhibiting expression or activity of DR5, and therefore it may prevent or treat diseases caused by overexpression of chemokine $CX_3CL1$ such as arthritis, cardiovascular diseases, cancer, HIV infection, primary biliary cirrhosis, renal disorder, allograft rejection, hypertension, eye disease, chronic pancreatitis, neuropathic pain, Sjogren syndrome, chronic obstructive pulmonary disease, emphysema, pulmonary fibrosis, atopic dermatitis, and lupus nephritic and the like, in particular, arthritis including rheumatoid arthritis.

One embodiment of the present invention provides a method for preventing or treating diseases caused by overexpression of chemokine $CX_3CL1$, comprising administering an inhibitor of expression or activity of DR5 to a subject in need of prevention or treatment caused by overexpression of chemokine $CX_3CL1$ in a therapeutically effective amount.

The inhibitor of expression or activity of DR5 may be siRNA, shRNA, miRNA, ribozyme, DNAzyme, PNA (peptide nucleic acids), anti-sense oligonucleotide, peptide, an antibody, an aptamer, natural extract or a chemical substance, and preferably, it may be an antibody or siRNA.

According to one specific embodiment of the present invention, the inhibitor of expression or activity of DR5 may bind to a CRD2 domain of DR5, or a CRD3 domain of DR5, or both a CRD2 domain and a CRD3 domain.

In addition, the antibody may bind to the 53th to 181th amino acid part in the amino acid sequence of SEQ ID NO: 1, and preferably, may bind to a CRD2 domain of DR5 consisting of the 101th to 120th amino acid sequence of SEQ ID NO: 1, or a CRD3 domain of DR5 consisting of the 143th to 160th amino acid sequence of SEQ ID NO: 1, or both the CRD2 and CRD3 domains.

One other embodiment of the present invention provides a use for prevention or treatment of diseases caused by overexpression of chemokine $CX_3CL1$ of an inhibitor of expression or activity of DR5.

The inhibitor of expression or activity of DR5 may be siRNA, shRNA, miRNA, ribozyme, DNAzyme, PNA (peptide nucleic acids), anti-sense oligonucleotide, peptide, an antibody, an aptamer, natural extract or a chemical substance, and preferably, it may be an antibody or siRNA.

According to one specific embodiment of the present invention, the inhibitor of expression or activity of DR5 may bind to a CRD2 domain of DR5, or a CRD3 domain of DR5, or both a CRD2 domain and a CRD3 domain.

In addition, the antibody may bind to the 53th to 181th amino acid part in the amino acid sequence of SEQ ID NO: 1, and preferably, may bind to a CRD2 domain of DR5 consisting of the 101th to 120th amino acid sequence of SEQ ID NO: 1, or a CRD3 domain of DR5 consisting of the 143th to 160th amino acid sequence of SEQ ID NO: 1, or both the CRD2 and CRD3 domains.

Thus, the technology of prevention and/or treatment of inflammation and diseases caused by overexpression of chemokine $CX_3CL1$, comprising the inhibitor of expression or activity of DR5 proposed herein as an active ingredient, and the technology of screening of a novel chemokine expression inhibitor using the same can not only effectively prevent occurrence of diseases caused by overexpression of chemokine $CX_3CL1$, but also obtain an excellent therapeutic effect even after some progress, and therefore they are very useful technologies for treating a lot of suffering patients, and they may be usefully used in investigation and development of a prophylactic or therapeutic agent of diseases caused by overexpression of chemokine $CX_3CL1$.

On the other hand, in other embodiment of the present invention, a method for decreasing expression of chemokine $CX_3CL1$ by administering a DR5 inhibitor to a patient in need of reduction of chemokine expression or a cell where chemokine is overexpressed may be provided, and also, a method of preventing or treating inflammation and diseases caused by overexpression of chemokine $CX_3CL1$, particularly, arthritis, by administering a DR5 inhibitor to a cell where chemokine $CX_3CL1$ is overexpressed.

The DR5 inhibitor is not particularly limited, unless it is a substance inhibiting expression of DR5 gene or inhibiting activity of DR5 protein, and the DR5 inhibitor may be siRNA, shRNA, miRNA, ribozyme, DNAzyme, PNA (peptide nucleic acids), anti-sense oligonucleotide, peptide, an antibody, an aptamer, natural extract or a chemical substance.

Advantageous Effects

The present invention can effectively prevent and treat diseases caused by overexpression of chemokine $CX_3CL1$, by reducing expression of $CX_3CL1$ that is one of inflammatory cytokines, by inhibiting binding between FasL and DR5 on a cell surface using an agent controlling DR5 expression or activity, for example, an inhibitor.

BRIEF DESCRIPTION OF THE DRAWINGS

FIG. 7a shows huDR5-CRD2 and huDR5-CRD3 which are candidate sites where huDR5 protein amino acid sequence (SEQ ID NO: 1) and sFasL are expected to bind, and the 111th, 114th, 119th, 120th, 148th, 150th, 153rd and 156th amino acids are Alanine-substituted mutation occurring sites.

FIG. 7b shows the 1st to 840th sequence of SEQ ID NO: 4 that is the huDR5 DNA sequence, and the polynucleotide consisting of the 334th to 363rd sequence and the polynucleotide consisting of the 445th to 471st sequence are mutation occurring sites.

FIG. 8a shows immunogen sites of the huDR5-CRD2 and huDR5-CRD3 and DR5 FACS antibody, which are candidate sites where huDR5 protein amino acid sequence (SEQ ID NO: 1), sFasL are expected to bind.

DETAILED DESCRIPTION OF THE INVENTION

Figure 1:
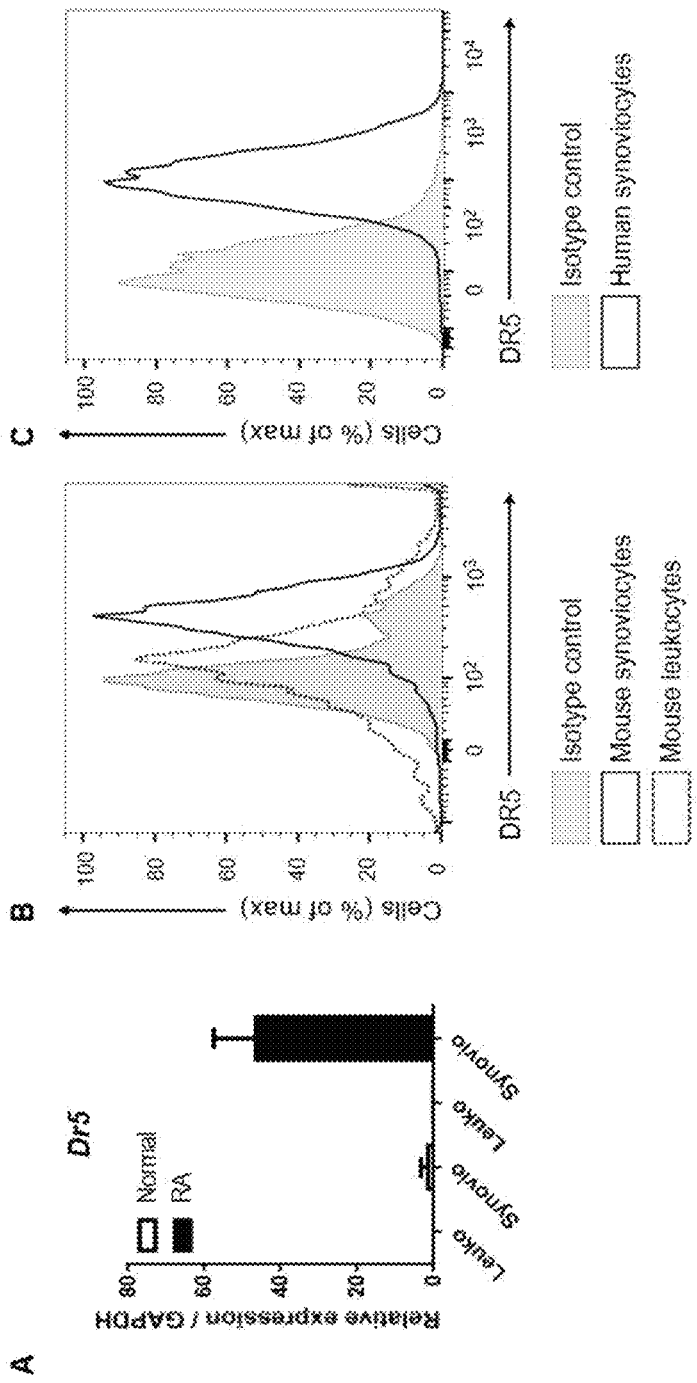
FIG. 1 (A) shows the result of confirming the expression of DR5 gene in each cell by real-time PCR, after isolating synovial cells (Adherent cell/Adh.) and normal immunocytes (Supernatant cell/Sup.) in the joint obtained from the normal mouse (Normal) and arthritis-induced mouse (RA), and FIG. 1 (B) shows the result of confirming the expression of DR5 surface protein in the synovial cells of the joint obtained from the arthritis-induced mouse (RA) by flow cytometry, and FIG. 1 (C) shows the result of confirming the expression of DR5 surface protein in hFLS (human fibroblast-like synoviocytes) by flow cytometry.

Hereinafter, the prevent invention will be described in more detail by examples. However, these examples are intended to illustrate the present invention only, and the scope of the present invention is not limited by these examples.

Example 1. Identification Membrane Protein which Binds to sFas Ligand (DR5)

Until now, it has been known that FasL binds to its receptor, Fas, and induces apoptosis of target cells, and thereby it causes joint inflammation. In addition, in the previous research of the present inventors, it has been revealed that FasL controls expression of chemokine with a new mechanism different from conventional inflammation induction of apoptosis of Fas-FasL, and also, it has been determined that FasL itself acts as chemokine attracting inflammatory cells. However, in the previous research, it has not been specifically revealed how FasL controls occurrence of inflammation by binding to which membrane protein in the new inflammation causing mechanism by FasL.

Accordingly, the present inventors have performed the protein identification experiment in order to find a protein binding to sFasL (soluble Fas Ligand) in the new inflammation causing mechanism by FasL.

At first, after obtaining synovium of an arthritis patient in vitro and then digesting with collagenase and culturing for 3 days, adherent cells were isolated to obtain human fibroblast-like synoviocytes (hFLS). By reacting biotinylated sFasL obtained by biotinylation of the obtained hFLS and recombinant human Fas ligand (R&D Systems 126-FL-010) with Sulfo-NHS-SS-Biotin—Thermo Scientific #21331, sFasL and hFLS targeting receptor protein were combined. Then, after cross-linking using a cross-linking agent (bis(sulfosuccinimidyl)suberate; BS3), cell lysis was conducted.

Then, to isolate sFasL-combined hFLS target protein, avidin purification was performed, and thereby the biotinylated sFas ligand recombinant protein and hFLS targeting receptor protein combined thereto were isolated together. After that, the sample was separated by SDS-PAGE and the gel was fractionized, and then peptides were extracted by the in-gel digestion method.

After analyzing the extracted peptides repeatedly twice using high resolution Hybrid quadrupole-orbitrap mass spectrometer, proteins which were not shown in the control group (Biotinylated Fc) and were shown only in the experimental group at least once were selected using SEQUEST algorithm. Proteins known to be present in cell membrane or extracellular matrix among selected proteins were sorted using classification by Uniprot database, and among them, DR5 was identified.

Example 2. Confirmation of Expression of DR5 Surface Protein in hFLS and Joint Synovial Cells of Arthritis-Induced Mouse In order to confirm the expression of DR5 surface protein in human-derived FLS (hFLS) and joint synovial cells of the arthritis-induced mouse, flow cytometry and real-time PCR were conducted. In real-time PCR, Applied Biosystems 7500 Real Time PCR System was used, and F: GGGCCACAGGGACACCTT (SEQ ID NO: 7)/R: GCATCTCGCCCGGTTTT (SEQ ID NO: 8) were used as primers, and they were reacted by 40 cycles of 50° C. for 2 minutes, 95° C. for 2 minutes, 95° C. for 15 seconds and then 60° C. for 1 minutes.

Then, after isolating synovial cells (Adherent cell/Adh.) and normal immunocytes (Supernatant cell/Sup.) in the joint obtained from the normal mouse (Normal) and arthritis-induced mouse (RA), respectively, expression of DR5 gene was compared in each cell. The experimental result was shown in FIG. 1.

As confirmed in FIG. 1 (A), the relative expression of DR5 surface protein in synovial cells of the joint obtained from the arthritis-induced mouse was increased than that in the normal mouse, and as confirmed by the flow cytometry result of FIG. 1 (B) and (C), it was confirmed that the DR5 surface protein was expressed in the arthritis-induced mouse synovial cells (Adherent cells) and hFLS.

Therefore, it could be seen that the expression of DR5 surface protein was increased in hFLS and cells obtained from a joint of arthritis-induced mouse, specifically in synovial cell, compared to the normal mouse.

Example 3. Confirmation of FasL-DR5 Intercombination 3-1. DR5 Antibody Treatment In order to confirm whether FasL and membrane protein DR5 actually bind, an anti-DR5 antibody (R&D systems AF631) was treated to hFLS to interrupt binding to cell surface DR5 of FasL.

Figure 2:
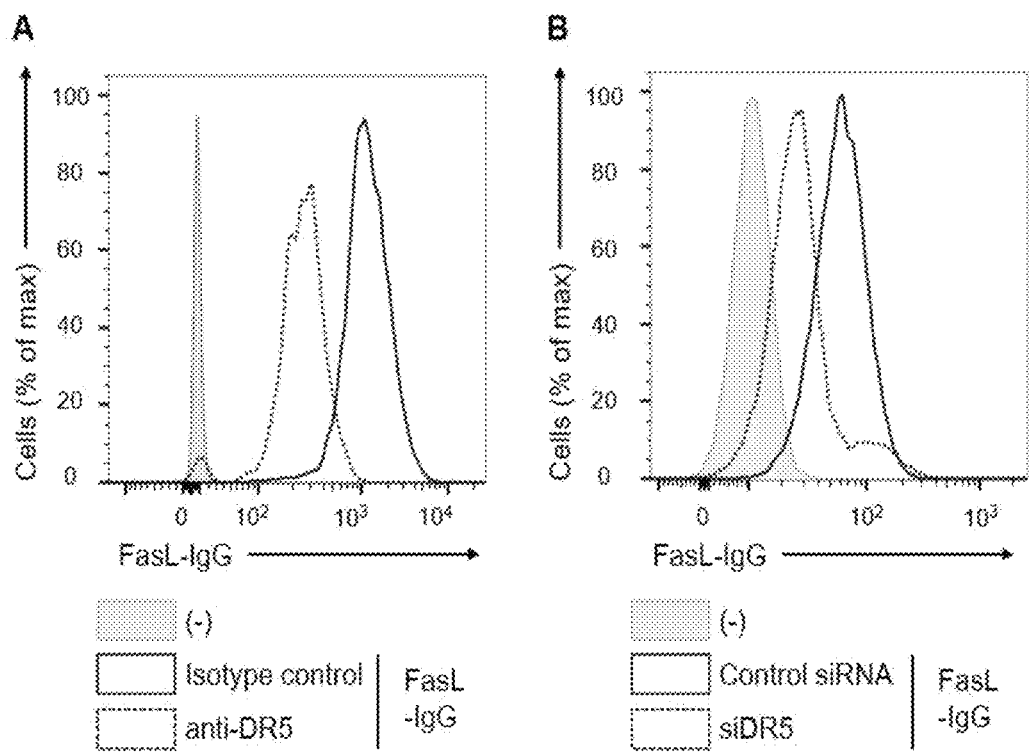
FIG. 2 shows the experimental result for confirming FasL-DR5 intercombination, and FIG. 2 (A) shows the result of verifying the interaction of FasL-DR5 by confirming that FasL-IgG binding is inhibited, when FasL binding to hFLS is inhibited by treating an anti-DR5 antibody, and FIG. 2 (B) is the result of confirming the IgG signal strength on the cell surface treated with IgG-combined FasL after DR5 knock down in hFLS by treating siRNA by flow cytometry.

Then, IgG-combined FasL was treated, and the IgG signal strength on the surface was confirmed by flow cytometry, and the result was shown in FIG. 2 (A). As could be seen in FIG. 2 (A), it could be seen that the signal strength by IgG was decreased when the anti-DR5 antibody was treated, and FasL-DR5 binding was reduced when the DR5 activity was inhibited by the anti-DR5 antibody.

3-2. Knock-Down Using siRNA Against DR5

In order to confirm whether FasL and membrane protein DR5 actually bind, siRNA (Sigma Aldrich MISSION siRNA; SASI_Hs01_00040567) was treated to hFLS, and using an electroporator (Neon transfection system, Thermo Fisher Scientific), expression of DR5 was knocked-down.

Then, after treating IgG-combined FasL, the IgG signal strength on the surface was confirmed by flow cytometry, and the result was shown in FIG. 2 (B). As could be seen in FIG. 2 (B), it could be seen that the signal strength by IgG was decreased when siRNA was treated, that is the signal strength by IgG was decreased as binding of Fas ligands was reduced, when expression of DR5 was reduced on the hFLS surface.

From the above results, it was confirmed that FasL and DR5 interactively bound specifically each other.

Figure 3:
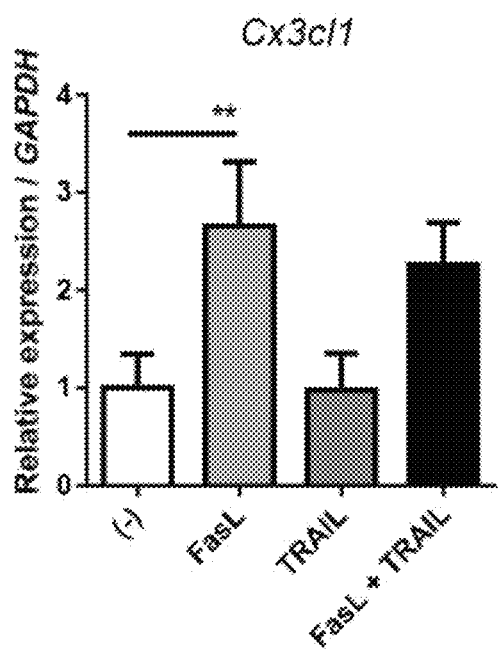
FIG. 3 shows the result of confirming secretion of CX$_3$CL1 by ELISA after treating FasL and TRAIL to hFLS alone or in combination.

Example 4. Confirmation of Increase of Chemokine $CX_3CL1$ Expression by FasL DR5 Binding In order to confirm chemokine where its expression is increased by FasL-DR5 binding, 200 ng/ml of each of FasL and TRAIL was treated to hFLS alone or in combination for 24 hours, and then the secretion of $CX_3CL1$ was confirmed according to the protocol provided by the manufacturer of ELISA (R&D systems DY365), and the result was shown in FIG. 3. As could be seen in FIG. 3, it was confirmed that the amount of $CX_3CL1$ was not increased when TRAIL known as a common ligand of DR5 was treated, but the amount of $CX_3CL1$ was increased when FasL was treated.

From that, it could be seen that the expression of chemokine $CX_3CL1$ was increased in hFLS by binding of FasL and DR5. It was confirmed that $CX_3CL1$ was one of chemokines causing inflammation, and facilitated the secretion of $CX_3CL1$ of hFLS cells during FasL-DR5 binding to cause inflammation.

Example 5. Confirmation of Decrease of Chemokine Expression by FasL-DR5 Inhibition In order to confirm whether the secretion of chemokine $CX_3CL1$ which is secreted when FasL is treated is decreased, when the interaction of FasL and DR5 is inhibited, the following experiment was performed.

5-1. DR5 Antibody Treatment

Figure 4:
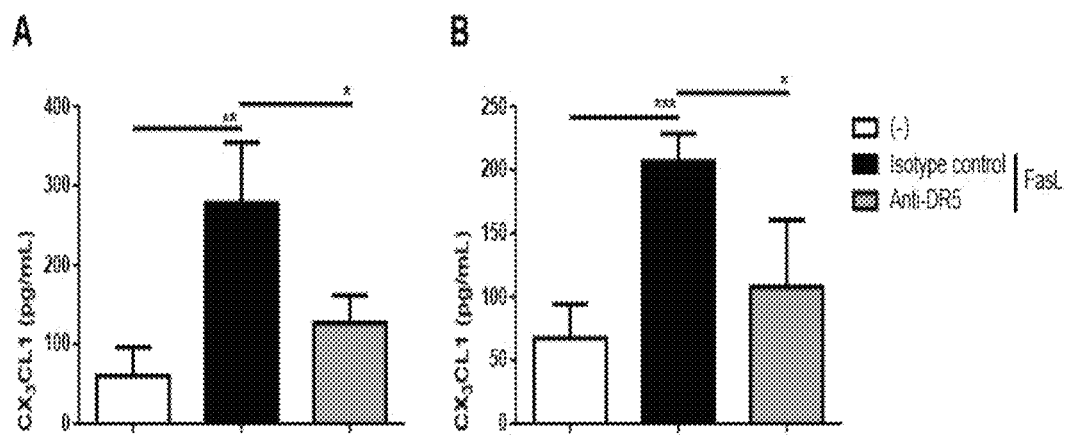
FIG. 4 (A) shows the result of measuring the amount of secreted CX$_3$CL1 by ELISA after inhibiting the interaction of FasL and DR5 by treating an anti-DR5 antibody to hFLS, and FIG. 4 (B) shows the result of measuring the amount of secreted CX$_3$CL1 by ELISA, after treating an anti-DR5 antibody to mouse synovial cells and then treating FasL.

After treating an antibody against 0.5 ug/ml of DR5 (R&D Systems AF631) to hFLS or mouse synovial cells for 1 hour and treating FasL 200 ng/mL, the amount of $CX_3CL1$ secreted was confirmed by ELISA, and the result was shown in FIG. 4. FIG. 4 (A) shows the treatment of the DR5 antibody to hFLS and the expression of $CX_3CL1$ was reduced in the anti-DR5 than Isotype (Goat IgG, R&D Systems AB-108-C), and FIG. 4 (B) shows the treatment of the anti-DR5 antibody to mouse synovial cells and it could be seen that the expression of $CX_3CL1$ in the anti-DR5 was also reduced.

5-2. siDR5 Knock-Down siRNA (Sigma Aldrich MISSION siRNA; SASI_Hs01_00040567) was treated to hFLS, and the expression of DR5 was knocked-down using an electroporator (Neon transfection system, Thermo Fisher Scientific), and as a result, as could be seen in FIG. 5 (A), it was confirmed that the expression of cell surface DR5 surface protein of hFLS was reduced by DR5 siRNA treatment.

Figure 5:
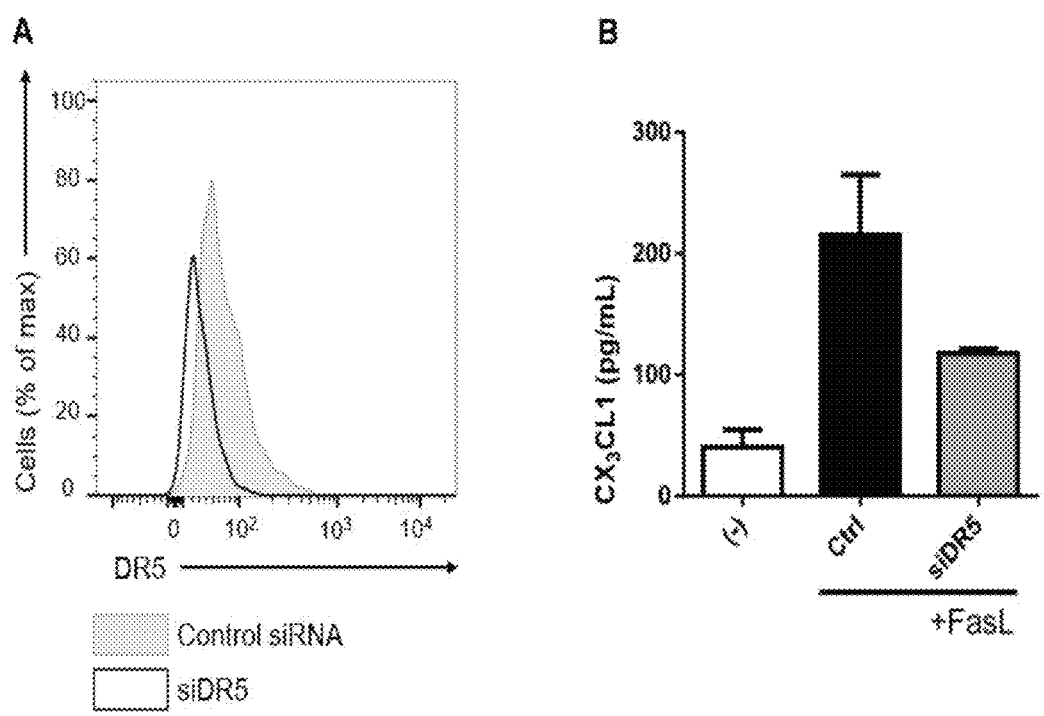
FIG. 5 (A) is a graph showing the result of reduced expression of DR5 surface protein on the cell surface of hFLS due to DR5 siRNA treatment, and FIG. 5 (B) is a graph showing the result of reduced secretion of CX$_3$CL1 in hFLS due to DR5 siRNA treatment.

Then, after treating FasL 200 ng/mL for 24 hours, and the amount of secreted $CX_3CL1$ was confirmed by ELISA, and as a result, as could be seen in FIG. 5 (B), it was confirmed that the amount of $CX_3CL1$ secreted by FasL treatment was decreased compared to the control group.

Taken the above results together, it could be seen that FasL bound to DR5 and the expression of $CX_3CL1$ was increased by this DR5 binding, and when interrupting FasL-DR5 interaction, the expression of $CX_3CL1$ was reduced. Thereby, it could be confirmed that when the DR5 antibody was treated, or DR5 was knocked-down to interrupt binding between DR5 and FasL, the expression of intracellular inflammation causing chemokine $CX_3CL1$ was reduced to inhibit inflammation occurrence, and it was effective in inhibiting arthritis symptoms not only in the early stage of occurrence of inflammation, particularly arthritis, but also after occurrence.

Example 6. Test of Alleviation of Arthritis Symptoms when Injecting the Anti-DR5 Antibody In order to confirm the alleviation of arthritis symptoms when injecting the anti-DR5 antibody to the arthritis mouse model induced by FasL, at first, serum was collected and prepared from blood in FasL deficient gld mouse (Central experimental animal) and K/B×N mouse that arthritis was naturally caused (obtained by crossbreeding KRN TCR transgenic mouse and NOD mouse provided from Drs. D. Mathis and C. Benoist of Harvard medical school, Boston, MA).

To the gld mouse, 1) K/B×N serum obtained above was injected (−), and 2) K/B×N serum and sFas ligand ((−)+sFas ligand)) was injected, and 3) K/B×N serum, sFas ligand and an anti-DR5 antibody (anti-DR5) were injected for 10 days, and the thickness of each joint was measured with a caliper (Manostat, Switzerland), and a clinical index was measured.

The clinical index referred to the followings:
0: no joint swelling,
1: swelling of one finger joint,
2: mild swelling of wrist or ankle,
3: severe swelling of wrist or ankle.

Figure 6:
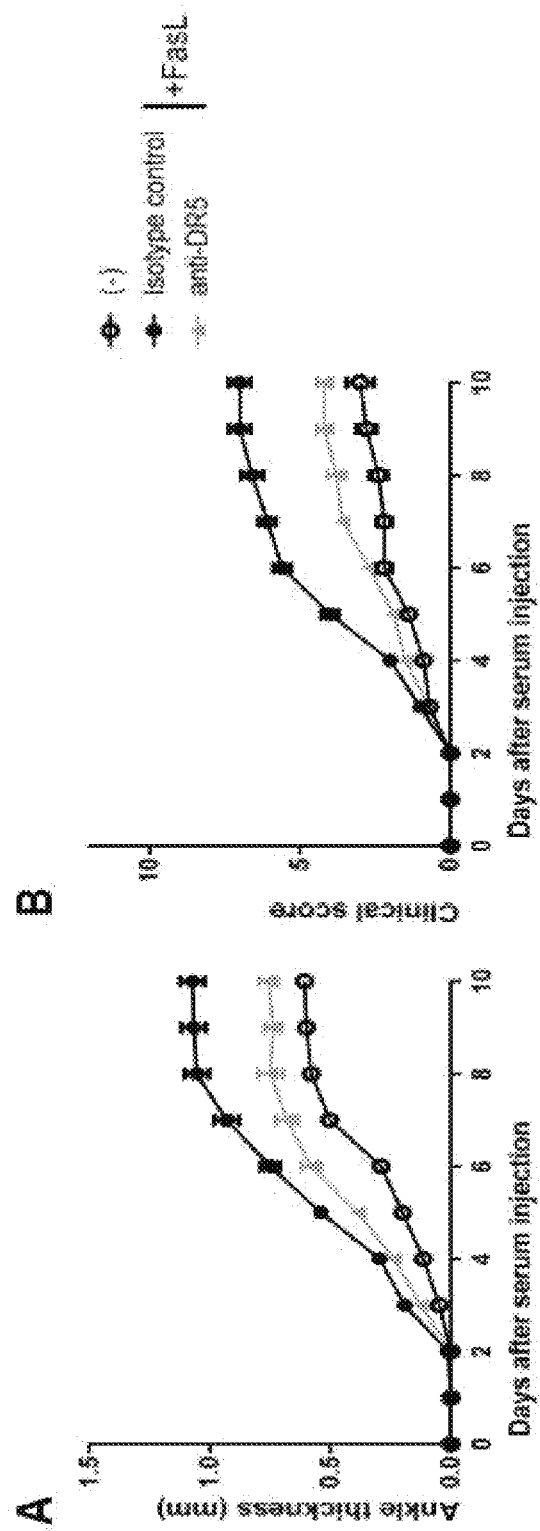
FIG. 6 shows the result of confirming that the disease symptoms induced by sFasL injection, when sFasL is injected and an anti-DR5 antibody is injected at the same time to a FasL-mutated gld mouse which is a FasL deficient mouse. It shows the changes of arthritis symptoms in gld mouse treated with K/BxN serum, gld mouse treated with K/BxN serum and sFasL, and gld mouse treated with K/BxN serum, sFas ligand and anti-DR5 antibody (anti-DR5), and (A) is the graph measuring the thickness of the joint and (B) is the graph measuring clinical indexes.

The thickness of the joint and the clinical index measured as above were shown in FIG. 6. As confirmed in FIG. 6 (A), when the serum and sFasL were treated to the gld mouse, the joint began to be swell from the 4th day and the highest index could be observed at day 9~10. However, when the serum and sFasL and the anti-DR5 were treated together to the gld mouse, little swelling of the joint could be observed. In addition, as confirmed in FIG. 6 (B), also in case of the clinical index, when treating sFasL and anti-DR5 together to the gld mouse, the clinical index remained at 3~4 points, and little swelling of the joint could be observed.

From the above results, it could be confirmed that the blockage of binding of DR5-FasL by anti-DR5 treatment inhibited the inflammation reaction, and it could be used as an agent for preventing and treating inflammation including arthritis.

Example 7. Confirmation of sFasL-DR5 Binding Sites Through DR5 Mutagenesis

In order to confirm the binding sites of sFasL and DR5, huDR5 (SEQ ID NO: 1 in Table 1)-cloned piRES3-Puro vector was used as a template, and using Overlap PCR method, in the candidate sites where sFasL was expected to bind in the huDR5 protein amino acid sequence (See FIG. 7a) (selecting sites where the ligand of DR5, TRAIL binds conventionally as the candidate sites), huDR5-CRD2 (334~363 in the total sequence) or huDR5-CRD3 (445~471 in the total sequence), the amino acids shown in blue in FIG. 7b were substituted with alanine and then were cloned, to prepare huDR5 mutation DNA (See FIG. 7b and Table 1).

Figure 8B:
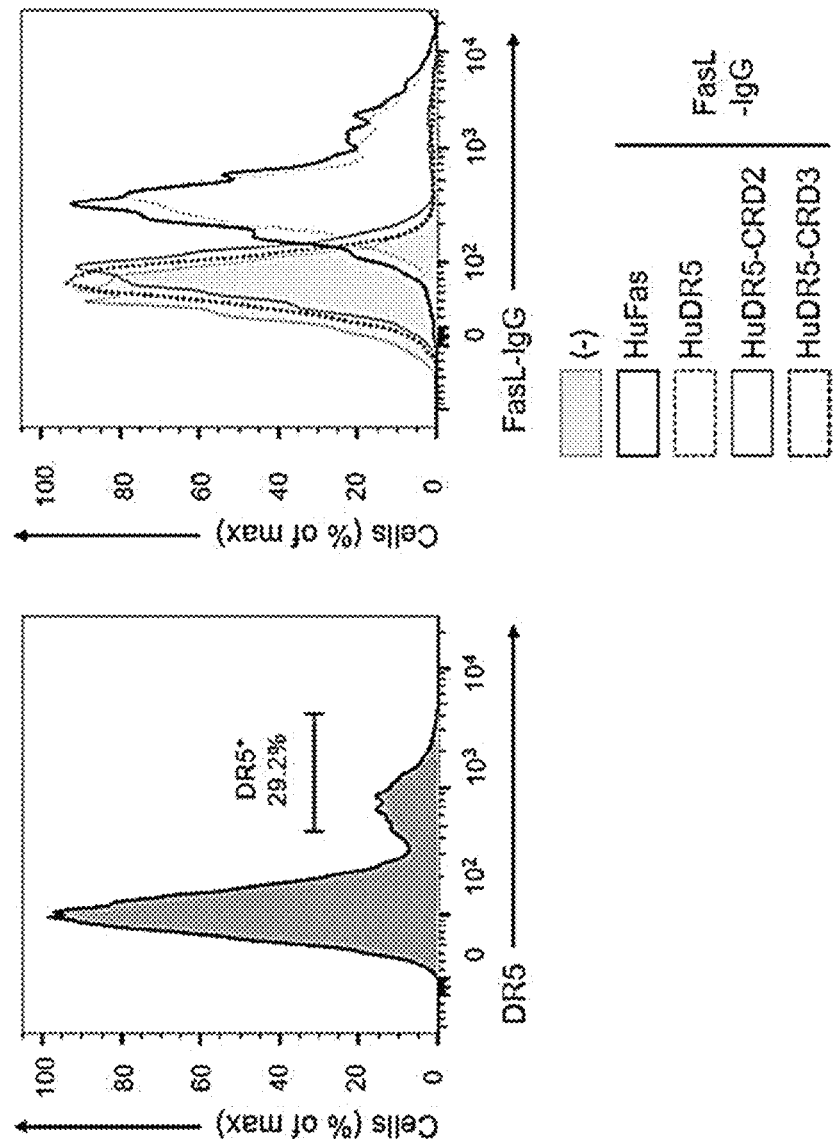
FIG. 8b shows the result of performing flow cytometry using human FasL where an immunoglobulin (IgG) that binds to huDR5 is combined, after expressing DR5 where huDR5-CRD2 or huDR5-CRD3 is mutated.

After transfecting mutated huDR5 DNA to mouse cells and expressing each of DR5 where huDR5-CRD2 was mutated (Table 1, SEQ ID NO: 4), or DR5 where huDR5-CRD3 was mutated (Table 1, SEQ ID NO: 5), flow cytometry was performed using human FasL where an immunoglobulin (IgG) binding only to cells expressing huDR5 was combined (huFasL-IgG), and the result was shown in FIG. 8b.

As could be seen in FIG. 8b, huFasL-IgG did not bind to huDR5 where CRD2 or CRD3 was mutated, and therefrom, it could be confirmed that the binding sites between FasL-DR5 bound using CRD3 and CRD3 of DR5 similar to TRAIL.

TABLE 1

| Classification | Sequence | SEQ ID NO |
|---|---|---|
| huDR5 Protein | MEQRGQNAPAASGARKRHGP GPREARGARPGPRVPKTLVL VVAAVLLVSAESALITQQDL APQQRAAPQQKRSSPSEGLC PPGHHISEDGRDCISCKYGQ DYSTHWNDLLFCLRCTRCDS GEVELSPCTTTRNTVCQCEE GTFREEDSPEMCRKCRTGCP RGMVKVGDCTPWSDIECVHK ESGIIIGVTVAAVVLIVAVF VCKSLLWKKVLPYLKGICSG GGGDPERVDRSSQRPGAEDN | 1 |
| Mutation huDR5-CRD2 Protein | MEQRGQNAPAASGARKRHGP GPREARGARPGPRVPKTLVL VVAAVLLVSAESALITQQDL APQQRAAPQQKRSSPSEGLC PPGHHISEDGRDCISCKYGQ DYSTHWNDLLACLACTRCAA GEVELSPCTTTRNTVCQCEE GTFREEDSPEMCRKCRTGCP RGMVKVGDCTPWSDIECVHK ESGIIIGVTVAAVVLIVAVF VCKSLLWKKVLPYLKGICSG GGGDPERVDRSSQRPGAEDN VLNEIVSILQPTQVPEQEME VQEPAEPTGVNMLSPGESEH LLEPAEAERSQRRRLLVPAN EGDPTETLRQCFDDFADLVP FDSWEPLMRKLGLMDNEIKV AKAEAAGHRDTLYTMLIKWV NKTGRDASVHTLLDALETLG ERLAKQKIEDHLLSSGKFMY LEGNADSAMS | 2 |
| Mutation huDR5-CRD3 Protein | MEQRGQNAPAASGARKRHGP GPREARGARPGPRVPKTLVL VVAAVLLVSAESALITQQDL APQQRAAPQQKRSSPSEGLC PPGHHISEDGRDCISCKYGQ DYSTHWNDLLFCLRCTRCDS GEVELSPCTTTRNTVCQCEE GTFREEDAPAMCAKCATGCP RGMVKVGDCTPWSDIECVHK ESGIIIGVTVAAVVLIVAVF VCKSLLWKKVLPYLKGICSG GGGDPERVDRSSQRPGAEDN VLNEIVSILQPTQVPEQEME VQEPAEPTGVNMLSPGESEH LLEPAEAERSQRRRLLVPAN EGDPTETLRQCFDDFADLVP FDSWEPLMRKLGLMDNEIKV AKAEAAGHRDTLYTMLIKWV NKTGRDASVHTLLDALETLG ERLAKQKIEDHLLSSGKFMY LEGNADSAMS | 3 |
| huDR5 DNA | atggaacaacggggacagaa cgccccggccgcttcggggg cccggaaaaggcacggccca ggacccagggaggcgcgggg agccaggcctgggccccggg tccccaagacccttgtgctc gttgtcgccgcggtcctgct gttggtctcagctgagtctg ctctgatcacccaacaagac ctagctccccagcagagagc ggcccacaacaaaagaggt ccagcccctcagagggattg tgtccacctggacaccatat ctcagaagacggtagagatt gcatctcctgcaaatatgga caggactatagcactcactg gaatgacctccttttctgct tgcgctgcaccaggtgtgat tcaggtgaagtggagctaag tccctgcaccacgaccagaa acacagtgtgtcagtgcgaa gaaggcacttccgggaaga agattctcctgagatgtgcc ggaagtgccgcacagggtgt cccagagggatggtcaaggt cggtgattgtacaccctgga gtgacatcgaatgtgtccac aaagaatcaggcatcatcat aggagtcacagttgcagccg tagtcttgattgtggctgtg tttgtttgcaagtctttact gtggaagaaagtccttcctt acctgaaaggcatctgctca ggtggtggtgggaccctga gcgtgtggacagaagctcac aacgacctggggctgaggac aatgtcctcaatgagatcgt gagtatcttgcagcccaccc aggtccctgagcaggaaatg gaagtccaggagccagcaga gccaacaggtgtcaacatgt tgtcccccggggagtcagag catctgctggaaccggcaga agctgaaaggtctcagagga ggaggctgctggttccagca aatgaaggtgatcccactga gactctgagacagtgcttcg atgactttgcagacttggtg cccttttgactcctgggagcc gctcatgaggaagttgggcc tcatggacaatgagataaag gtggctaaagctgaggcagc gggccacagggacaccttgt acacgatgctgataaagtgg | 4 |

TABLE 1-continued

| Classification | Sequence | SEQ ID NO |
|---|---|---|
| | gtcaacaaaaccgggcgaga tgcctctgtccacacctgc tggatgccttggagacgct ggagagagacttgccaagca gaagattgaggaccacttgt tgagctctggaaagttcatg tatctagaaggtaatgcaga ctctgccatgtcctaa | |
| Mutation huDR5-CRD2 DNA | atggaacaacggggacagaa cgccccggccgcttcggggg cccggaaaaggcacggccca ggacccaggggaggcgcgggg agccaggcctgggcccccggg tccccaagacccttgtgctc gttgtcgccgcggtcctgct gttggtctcagctgagtctg ctctgatcacccaacaagac ctagctccccagcagagagc ggccccacaacaaaagaggt ccagcccctcagagggattg tgtccacctggacaccatat ctcagaagacggtagagatt gcatctcctgcaaatatgga caggactatagcactcactg gaatgacctccttgcctgct tggcctgcaccacgtgtgct gcaggtgaagtggagctaag tccctgcaccacgaccagaa acacagtgtgtcagtgcgaa gaaggcaccttccgggaaga agattctcctgagatgtgcc ggaagtgccgcacagggtgt cccagagggatggtcaaggt cggtgattgtacaccctgga gtgacatcgaatgtgtccac aaagaatcaggcatcatcat aggagtcacagttgcagccg tagtcttgattgtggctgtg tttgtttgcaagtctttact gtggaagaaagtccttcctt acctgaaaggcatctgctca ggtggtggtggggacccctga gcgtgtggacagaagctcac aacgacctggggctgaggac aatgtcctcaatgagatcgt gagtatcttgcagcccaccc aggtccctgagcaggaaatg gaagtccaggagccagcaga gccaacaggtgtcaacatgt tgtccccggggagtcagag catctgctggaaccggcaga agctgaaaggtctcaggaga ggaggctgctggttccagca aatgaaggtgatcccactga gactctgagacagtgcttcg atgactttgcagacttggtg ccctttgactcctgggagcc gctcatgaggaagttgggcc tcatggacaatgagataaag gtggctaaagctgaggcagc gggccacagggacaccttgt acacgatgctgataaagtgg gtcaacaaaaccgggcgaga tgcctctgtccacacctgc tggatgccttggagacgct ggagagagacttgccaagca gaagattgaggaccacttgt tgagctctggaaagttcatg tatctagaaggtaatgcaga ctctgccatgtcctaa | 5 |
| Mutation huDR5-CRD3 DNA | atggaacaacggggacagaa cgccccggccgcttcggggg cccggaaaaggcacggccca ggacccaggggaggcgcgggg agccaggcctgggcccccggg tccccaagacccttgtgctc gttgtcgccgcggtcctgct gttggtctcagctgagtctg ctctgatcacccaacaagac ctagctccccagcagagagc ggccccacaacaaaagaggt ccagcccctcagagggattg tgtccacctggacaccatat ctcagaagacggtagagatt gcatctcctgcaaatatgga caggactatagcactcactg gaatgacctccttttctgct tgcgctgcaccaggtgtgat tcaggtgaagtggagctaag tccctgcaccacgaccagaa acacagtgtgtcagtgcgaa gaaggcaccttccgggaaga agatgctcctgcgatgtgcg cgaagtgcgccacagggtgt cccagagggatggtcaaggt cggtgattgtacaccctgga gtgacatcgaatgtgtccac aaagaatcaggcatcatcat aggagtcacagttgcagccg tagtcttgattgtggctgtg tttgtttgcaagtctttact gtggaagaaagtccttcctt acctgaaaggcatctgctca ggtggtggtggggacccctga gcgtgtggacagaagctcac aacgacctggggctgaggac aatgtcctcaatgagatcgt gagtatcttgcagcccaccc aggtccctgagcaggaaatg gaagtccaggagccagcaga gccaacaggtgtcaacatgt tgtccccggggagtcagag catctgctggaaccggcaga agctgaaaggtctcaggaga ggaggctgctggttccagca aatgaaggtgatcccactga gactctgagacagtgcttcg atgactttgcagacttggtg ccctttgactcctgggagcc gctcatgaggaagttgggcc tcatggacaatgagataaag gtggctaaagctgaggcagc gggccacagggacaccttgt acacgatgctgataaagtgg gtcaacaaaaccgggcgaga tgcctctgtccacacctgc tggatgccttggagacgct ggagagagacttgccaagca gaagattgaggaccacttgt tgagctctggaaagttcatg tatctagaaggtaatgcaga ctctgccatgtcctaa | 6 |

The invention claimed is:

1. A method for treating a disease caused by overexpression of chemokine $CX_3CL1$ in a patient in need thereof, comprising administering a therapeutically effective amount of an inhibitor of expression or activity of DR5 to the patient, wherein the inhibitor of expression or activity of DR5 is a siRNA against DR5, and wherein the disease is arthritis.

* * * * *

SEQUENCE LISTING

<160> NUMBER OF SEQ ID NOS: 8

<210> SEQ ID NO 1
<211> LENGTH: 410
<212> TYPE: PRT
<213> ORGANISM: Artificial Sequence
<220> FEATURE:
<223> OTHER INFORMATION: wildtype HuDR5 protein

<400> SEQUENCE: 1

```
Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Val
        35                  40                  45

Ser Ala Glu Ser Ala Leu Ile Thr Gln Gln Asp Leu Ala Pro Gln Gln
50                  55                  60

Arg Ala Ala Pro Gln Gln Lys Arg Ser Ser Pro Ser Glu Gly Leu Cys
65                  70                  75                  80

Pro Pro Gly His His Ile Ser Glu Asp Gly Arg Asp Cys Ile Ser Cys
                85                  90                  95

Lys Tyr Gly Gln Asp Tyr Ser Thr His Trp Asn Asp Leu Leu Phe Cys
            100                 105                 110

Leu Arg Cys Thr Arg Cys Asp Ser Gly Glu Val Glu Leu Ser Pro Cys
        115                 120                 125

Thr Thr Thr Arg Asn Thr Val Cys Gln Cys Glu Glu Gly Thr Phe Arg
130                 135                 140

Glu Glu Asp Ser Pro Glu Met Cys Arg Lys Cys Arg Thr Gly Cys Pro
145                 150                 155                 160

Arg Gly Met Val Lys Val Gly Asp Cys Thr Pro Trp Ser Asp Ile Glu
                165                 170                 175

Cys Val His Lys Glu Ser Gly Ile Ile Ile Gly Val Thr Val Ala Ala
            180                 185                 190

Val Val Leu Ile Val Ala Val Phe Val Cys Lys Ser Leu Leu Trp Lys
        195                 200                 205

Lys Val Leu Pro Tyr Leu Lys Gly Ile Cys Ser Gly Gly Gly Gly Asp
210                 215                 220

Pro Glu Arg Val Asp Arg Ser Ser Gln Arg Pro Gly Ala Glu Asp Asn
225                 230                 235                 240

Val Leu Asn Glu Ile Val Ser Ile Leu Gln Pro Thr Gln Val Pro Glu
                245                 250                 255

Gln Glu Met Glu Val Gln Glu Pro Ala Glu Pro Thr Gly Val Asn Met
            260                 265                 270

Leu Ser Pro Gly Glu Ser Glu His Leu Leu Glu Pro Ala Glu Ala Glu
        275                 280                 285

Arg Ser Gln Arg Arg Arg Leu Leu Val Pro Ala Asn Glu Gly Asp Pro
290                 295                 300

Thr Glu Thr Leu Arg Gln Cys Phe Asp Asp Phe Ala Asp Leu Val Pro
305                 310                 315                 320

Phe Asp Ser Trp Glu Pro Leu Met Arg Lys Leu Gly Leu Met Asp Asn
                325                 330                 335

Glu Ile Lys Val Ala Lys Ala Glu Ala Ala Gly His Arg Asp Thr Leu
            340                 345                 350

Tyr Thr Met Leu Ile Lys Trp Val Asn Lys Thr Gly Arg Asp Ala Ser
```

```
              355                 360                 365
Val His Thr Leu Leu Asp Ala Leu Glu Thr Leu Gly Glu Arg Leu Ala
    370                 375                 380
Lys Gln Lys Ile Glu Asp His Leu Leu Ser Ser Gly Lys Phe Met Tyr
385                 390                 395                 400
Leu Glu Gly Asn Ala Asp Ser Ala Met Ser
                405                 410

<210> SEQ ID NO 2
<211> LENGTH: 410
<212> TYPE: PRT
<213> ORGANISM: Artificial Sequence
<220> FEATURE:
<223> OTHER INFORMATION: HuDR5 protein including mutated CRD2

<400> SEQUENCE: 2

Met Glu Gln Arg Gly Gln Asn Ala Pro Ala Ala Ser Gly Ala Arg Lys
1               5                   10                  15
Arg His Gly Pro Gly Pro Arg Glu Ala Arg Gly Ala Arg Pro Gly Pro
                20                  25                  30
Arg Val Pro Lys Thr Leu Val Leu Val Val Ala Ala Val Leu Leu Val
                35                  40                  45
Ser Ala Glu Ser Ala Leu Ile Thr Gln Gln Asp Leu Ala Pro Gln Gln
            50                  55                  60
Arg Ala Ala Pro Gln Gln Lys Arg Ser Ser Pro Ser Glu Gly Leu Cys
65                  70                  75                  80
Pro Pro Gly His His Ile Ser Glu Asp Gly Arg Asp Cys Ile Ser Cys
                    85                  90                  95
Lys Tyr Gly Gln Asp Tyr Ser Thr His Trp Asn Asp Leu Leu Ala Cys
                100                 105                 110
Leu Ala Cys Thr Arg Cys Ala Ala Gly Glu Val Glu Leu Ser Pro Cys
            115                 120                 125
Thr Thr Thr Arg Asn Thr Val Cys Gln Cys Glu Glu Gly Thr Phe Arg
            130                 135                 140
Glu Glu Asp Ser Pro Glu Met Cys Arg Lys Cys Arg Thr Gly Cys Pro
145                 150                 155                 160
Arg Gly Met Val Lys Val Gly Asp Cys Thr Pro Trp Ser Asp Ile Glu
                165                 170                 175
Cys Val His Lys Glu Ser Gly Ile Ile Ile Gly Val Thr Val Ala Ala
                180                 185                 190
Val Val Leu Ile Val Ala Val Phe Val Cys Lys Ser Leu Leu Trp Lys
            195                 200                 205
Lys Val Leu Pro Tyr Leu Lys Gly Ile Cys Ser Gly Gly Gly Gly Asp
        210                 215                 220
Pro Glu Arg Val Asp Arg Ser Ser Gln Arg Pro Gly Ala Glu Asp Asn
225                 230                 235                 240
Val Leu Asn Glu Ile Val Ser Ile Leu Gln Pro Thr Gln Val Pro Glu
                245                 250                 255
Gln Glu Met Glu Val Gln Glu Pro Ala Glu Pro Thr Gly Val Asn Met
                260                 265                 270
Leu Ser Pro Gly Glu Ser Glu His Leu Leu Glu Pro Ala Glu Ala Glu
            275                 280                 285
Arg Ser Gln Arg Arg Arg Leu Leu Val Pro Ala Asn Glu Gly Asp Pro
290                 295                 300
Thr Glu Thr Leu Arg Gln Cys Phe Asp Asp Phe Ala Asp Leu Val Pro
```

```
            305                 310                 315                 320
    Phe Asp Ser Trp Glu Pro Leu Met Arg Lys Leu Gly Leu Met Asp Asn
                    325                 330                 335

Glu Ile Lys Val Ala Lys Ala Glu Ala Ala Gly His Arg Asp Thr Leu
                    340                 345                 350

Tyr Thr Met Leu Ile Lys Trp Val Asn Lys Thr Gly Arg Asp Ala Ser
                    355                 360                 365

Val His Thr Leu Leu Asp Ala Leu Glu Thr Leu Gly Glu Arg Leu Ala
                370                 375                 380

Lys Gln Lys Ile Glu Asp His Leu Leu Ser Ser Gly Lys Phe Met Tyr
    385                 390                 395                 400

Leu Glu Gly Asn Ala Asp Ser Ala Met Ser
                    405                 410

<210> SEQ ID NO 3
<211> LENGTH: 410
<212> TYPE: PRT
<213> ORGANISM: Artificial Sequence
<220> FEATURE:
<223> OTHER INFORMATION: HuDR5 protein including mutated CRD3

<400> SEQUENCE: 3

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
                20                  25                  30

Arg Val Pro Lys Thr Leu Val Leu Val Val Ala Ala Val Leu Leu Val
                35                  40                  45

Ser Ala Glu Ser Ala Leu Ile Thr Gln Gln Asp Leu Ala Pro Gln Gln
            50                  55                  60

Arg Ala Ala Pro Gln Gln Lys Arg Ser Ser Pro Ser Glu Gly Leu Cys
65                  70                  75                  80

Pro Pro Gly His His Ile Ser Glu Asp Gly Arg Asp Cys Ile Ser Cys
                85                  90                  95

Lys Tyr Gly Gln Asp Tyr Ser Thr His Trp Asn Asp Leu Leu Phe Cys
                100                 105                 110

Leu Arg Cys Thr Arg Cys Asp Ser Gly Glu Val Glu Leu Ser Pro Cys
            115                 120                 125

Thr Thr Thr Arg Asn Thr Val Cys Gln Cys Glu Glu Gly Thr Phe Arg
            130                 135                 140

Glu Glu Asp Ala Pro Ala Met Cys Ala Lys Cys Ala Thr Gly Cys Pro
145                 150                 155                 160

Arg Gly Met Val Lys Val Gly Asp Cys Thr Pro Trp Ser Asp Ile Glu
                165                 170                 175

Cys Val His Lys Glu Ser Gly Ile Ile Ile Gly Val Thr Val Ala Ala
                180                 185                 190

Val Val Leu Ile Val Ala Val Phe Val Cys Lys Ser Leu Leu Trp Lys
            195                 200                 205

Lys Val Leu Pro Tyr Leu Lys Gly Ile Cys Ser Gly Gly Gly Gly Asp
            210                 215                 220

Pro Glu Arg Val Asp Arg Ser Ser Gln Arg Pro Gly Ala Glu Asp Asn
225                 230                 235                 240

Val Leu Asn Glu Ile Val Ser Ile Leu Gln Pro Thr Gln Val Pro Glu
                245                 250                 255

Gln Glu Met Glu Val Gln Glu Pro Ala Glu Pro Thr Gly Val Asn Met
```

```
                260                 265                 270
Leu Ser Pro Gly Glu Ser Glu His Leu Leu Glu Pro Ala Glu Ala Glu
            275                 280                 285

Arg Ser Gln Arg Arg Arg Leu Leu Val Pro Ala Asn Glu Gly Asp Pro
            290                 295                 300

Thr Glu Thr Leu Arg Gln Cys Phe Asp Asp Phe Ala Asp Leu Val Pro
305                 310                 315                 320

Phe Asp Ser Trp Glu Pro Leu Met Arg Lys Leu Gly Leu Met Asp Asn
                325                 330                 335

Glu Ile Lys Val Ala Lys Ala Glu Ala Ala Gly His Arg Asp Thr Leu
            340                 345                 350

Tyr Thr Met Leu Ile Lys Trp Val Asn Lys Thr Gly Arg Asp Ala Ser
            355                 360                 365

Val His Thr Leu Leu Asp Ala Leu Glu Thr Leu Gly Glu Arg Leu Ala
            370                 375                 380

Lys Gln Lys Ile Glu Asp His Leu Leu Ser Ser Gly Lys Phe Met Tyr
385                 390                 395                 400

Leu Glu Gly Asn Ala Asp Ser Ala Met Ser
                405                 410

<210> SEQ ID NO 4
<211> LENGTH: 1236
<212> TYPE: DNA
<213> ORGANISM: Artificial Sequence
<220> FEATURE:
<223> OTHER INFORMATION: DNA sequence of wildtype HuDR5 protein

<400> SEQUENCE: 4
atggaacaac ggggacagaa cgccccggcc gcttcggggg cccggaaaag gcacggccca     60
ggacccaggg aggcgcgggg agccaggcct gggcccccggg tccccaagac ccttgtgctc    120
gttgtcgccg cggtcctgct gttggtctca gctgagtctg ctctgatcac ccaacaagac    180
ctagctcccc agcagagagc ggcccacaa caaaagaggt ccagcccctc agagggattg     240
tgtccacctg acaccatat ctcagaagac ggtagagatt gcatctcctg caaatatgga     300
caggactata gcactcactg gaatgacctc ctttttctgct tgcgctgcac caggtgtgat    360
tcaggtgaag tggagctaag tccctgcacc acgaccagaa acacagtgtg tcagtgcgaa    420
gaaggcacct tccgggaaga agattctcct gagatgtgcc ggaagtgccg cacagggtgt    480
cccagaggga tggtcaaggt cggtgattgt acaccctgga gtgacatcga atgtgtccac    540
aaagaatcag gcatcatcat aggagtcaca gttgcagccg tagtcttgat tgtggctgtg    600
tttgtttgca agtctttact gtggaagaaa gtccttcctt acctgaaagg catctgctca    660
ggtggtggtg gggaccctga gcgtgtggac agaagctcac aacgacctgg ggctgaggac    720
aatgtcctca tgagatcgt gagtatcttg cagcccaccc aggtccctga gcaggaaatg    780
gaagtccagg agccagcaga gccaacaggt gtcaacatgt tgtcccccgg ggagtcagag    840
catctgctgg aaccggcaga agctgaaagg tctcagagga ggaggctgct ggttccagca    900
aatgaaggtg atcccactga gactctgaga gcagtgcttc gatgactttgc agacttggtg    960
ccctttgact cctgggagcc gctcatgagg aagttgggcc tcatggacaa tgagataaag   1020
gtggctaaag ctgaggcagc gggccacagg gacaccttgt acacgatgct gataaagtgg   1080
gtcaacaaaa ccgggcgaga tgcctctgtc cacaccctgc tggatgcctt ggagacgctg   1140
ggagagagac ttgccaagca gaagattgag gaccacttgt tgagctctgg aaagttcatg   1200
```

```
tatctagaag gtaatgcaga ctctgccatg tcctaa                             1236
```

<210> SEQ ID NO 5
<211> LENGTH: 1236
<212> TYPE: DNA
<213> ORGANISM: Artificial Sequence
<220> FEATURE:
<223> OTHER INFORMATION: DNA sequence of HuDR5 protein including mutated
      CRD2

<400> SEQUENCE: 5

```
atggaacaac ggggacagaa cgccccggcc gcttcggggg cccggaaaag gcacggccca     60
ggacccaggg aggcgcgggg agccaggcct gggccccggg tccccaagac ccttgtgctc    120
gttgtcgccg cggtcctgct gttggtctca gctgagtctg ctctgatcac ccaacaagac    180
ctagctcccc agcagagagc ggccccacaa caaaagaggt ccagcccctc agagggattg    240
tgtccacctg gacaccatat ctcagaagac ggtagagatt gcatctcctg caaatatgga    300
caggactata gcactcactg gaatgacctc cttgcctgct ggcctgcac cacgtgtgct     360
gcaggtgaag tggagctaag tcctgcacc acgaccagaa acacagtgtg tcagtgcgaa     420
gaaggcacct ccgggaaga agattctcct gagatgtgcc ggaagtgccg cacagggtgt    480
cccagaggga tggtcaaggt cggtgattgt acaccctgga gtgacatcga atgtgtccac    540
aaagaatcag gcatcatcat aggagtcaca gttgcagccg tagtcttgat tgtggctgtg    600
tttgtttgca gtctttact gtggaagaaa gtccttcctt acctgaaagg catctgctca    660
ggtggtggtg ggaccctga gcgtgtggac agaagctcac aacgacctgg ggctgaggac    720
aatgtcctca atgagatcgt gagtatcttg cagcccaccc aggtccctga gcaggaaatg    780
gaagtccagg agccagcaga gccaacaggt gtcaacatgt tgtcccccgg ggagtcagag    840
catctgctgg aaccggcaga agctgaaagg tctcagagga ggaggctgct ggttccagca    900
aatgaaggtg atccccactga gactctgaga cagtgcttcg atgactttgc agacttggtg    960
ccctttgact cctgggagcc gctcatgagg aagttgggcc tcatggacaa tgagataaag   1020
gtggctaaag ctgaggcagc gggccacagg gacaccttgt acacgatgct gataaagtgg    1080
gtcaacaaaa ccgggcgaga tgcctctgtc cacaccctgc tggatgcctt ggagacgctg   1140
ggagagagac ttgccaagca agaagattgag gaccacttgt tgagctctgg aaagttcatg   1200
tatctagaag gtaatgcaga ctctgccatg tcctaa                             1236
```

<210> SEQ ID NO 6
<211> LENGTH: 1236
<212> TYPE: DNA
<213> ORGANISM: Artificial Sequence
<220> FEATURE:
<223> OTHER INFORMATION: DNA sequence of HuDR5 protein including mutated
      CRD3

<400> SEQUENCE: 6

```
atggaacaac ggggacagaa cgccccggcc gcttcggggg cccggaaaag gcacggccca    60
ggacccaggg aggcgcgggg agccaggcct gggccccggg tccccaagac ccttgtgctc   120
gttgtcgccg cggtcctgct gttggtctca gctgagtctg ctctgatcac ccaacaagac   180
ctagctcccc agcagagagc ggccccacaa caaaagaggt ccagcccctc agagggattg   240
tgtccacctg acaccatat ctcagaagac ggtagagatt gcatctcctg caaatatgga   300
caggactata gcactcactg gaatgacctc cttttctgct tgcgctgcac caggtgtgat   360
tcaggtgaag tggagctaag tccctgcacc acgaccagaa acacagtgtg tcagtgcgaa   420
gaaggcacct tccgggaaga gatgctcct gcgatgtgcg cgaagtgcgc cacagggtgt   480
cccagaggga tggtcaaggt cggtgattgt acacctgga gtgacatcga atgtgtccac   540
aaagaatcag gcatcatcat aggagtcaca gttgcagccg tagtcttgat tgtggctgtg   600
tttgtttgca agtctttact gtggaagaaa gtccttcctt acctgaaagg catctgctca   660
ggtggtggtg ggaccctga gcgtgtggac agaagctcac aacgacctgg ggctgaggac   720
aatgtcctca atgagatcgt gagtatcttg cagcccaccc aggtccctga gcaggaaatg   780
gaagtccagg agccagcaga gccaacaggt gtcaacatgt tgtccccgg ggagtcagag   840
catctgctgg aaccggcaga agctgaaagg tctcagagga ggaggctgct ggttccagca   900
aatgaaggtg atcccactga gactctgaga cagtgcttcg atgactttgc agacttggtg   960
cccttt gact cctgggagcc gctcatgagg aagttgggcc tcatggacaa tgagataaag  1020
gtggctaaag ctgaggcagc gggccacagg gacaccttgt acacgatgct gataaagtgg  1080
gtcaacaaaa ccgggcgaga tgcctctgtc cacacctgc tggatgcctt ggagacgctg  1140
ggagagagac ttgccaagca gaagattgag gaccacttgt tgagctctgg aaagttcatg  1200
tatctagaag gtaatgcaga ctctgccatg tcctaa                            1236
```

<210> SEQ ID NO 7
<211> LENGTH: 18
<212> TYPE: DNA
<213> ORGANISM: Artificial Sequence
<220> FEATURE:
<223> OTHER INFORMATION: synthetic_Primer-F

<400> SEQUENCE: 7

```
gggccacagg gacacctt                                                  18
```

<210> SEQ ID NO 8
<211> LENGTH: 17
<212> TYPE: DNA
<213> ORGANISM: Artificial Sequence
<220> FEATURE:
<223> OTHER INFORMATION: synthetic_Primer-R

<400> SEQUENCE: 8

```
gcatctcgcc cggtttt                                                   17
```